United States Patent [19]

Blaser et al.

[11] Patent Number: 5,459,041

[45] Date of Patent: Oct. 17, 1995

[54] *CAMPYLOBACTER PYLORI* ANTIGENS AND USES THEREOF FOR DETECTION OF *CAMPYLOBACTER PYLORI* INFECTION

[75] Inventors: Martin J. Blaser, New York, N.Y.; Guillermo I. Perez-Perez, Denver, Colo.

[73] Assignee: Enteric Research Laboratories, Inc., Denver, Colo.

[21] Appl. No.: 158,003

[22] Filed: Feb. 18, 1988

[51] Int. Cl.$^6$ ........................................ G01N 33/53
[52] U.S. Cl. ................. 435/7.21; 435/7.3; 435/7.92; 435/7.93; 435/7.94; 435/7.95; 435/961; 435/974; 435/975; 436/518; 436/527; 436/528; 436/529; 436/531; 436/533; 436/547; 436/804; 530/350; 530/413; 530/806; 530/810; 530/825
[58] Field of Search .................... 435/7, 12, 174, 435/810, 7.21, 7.3, 7.9, 7.92–7.95, 975, 961, 974; 436/501, 518, 527, 529, 531, 533, 547, 804, 808, 811, 813; 530/350, 413, 806, 810, 825; 424/92

[56] References Cited

U.S. PATENT DOCUMENTS

| | | | |
|---|---|---|---|
| 4,882,271 | 11/1989 | Evans et al. | 435/7 |
| 5,108,892 | 4/1992 | Burke et al. | 435/6 |

FOREIGN PATENT DOCUMENTS

| | | |
|---|---|---|
| 8601808 | 3/1986 | WIPO . |
| 8701119 | 2/1987 | WIPO . |

OTHER PUBLICATIONS

B. Marshall et al., The Lancet, Aug. 4, 1984, p. 281.
E. Hoftmann, Chromatography (Reinhold Publishing Corporation, New York), 1961, pp. 378–427.
A. Chrambach, The Practice of Quantitative Gel Electrophoresis in Advanced Methods in the Biological Sciences, (1985), pp. 7–8, 111–128 and 178–185.
D. Newell et al., Journal of General Microbiology, vol. 130, pp. 1201–1208 (1984).
F. Bolton et al., Journal of Clinical Pathology, vol. 42, pp. 723–726 (1989).
B. Davis et al., Microbiology, Third Edition (Harper & Row, Publishers, Inc., 1980), pp. 98–102.
G. Tortora et al., Microbiology, An Introduction (The Benjamin/Cummings Publishing Company, Inc., 1982), pp. 79–81.
M. Pelczar, Jr. et al., Microbiology, fourth edition, (McGraw–Hill Book Company, 1977), pp. 83–87.
M. Pelczar, Jr. et al., Microbiology, second edition, (McGraw Hill Book Company, 1965), pp. 61–64.
N. Tutz (ed), Textbook of Clinical Chemistry, (W. B. Saunders Company, 1986), pp. 290–294, 310–311, 356–380, 395–399.
Biological Abstract 87(6):59552; Hirschl et al., "Comparison of different antigen preparations in . . . *Campylobacter pylori*", Eur. J. Clin. Microbiol. Infect. Dis., 74(4):570–575, 1988.
European Search Report, European Patent Office, Apr. 3, 1991, Appln. No. 89400464.7.

(List continued on next page.)

*Primary Examiner*—Carol A. Spiegel
*Attorney, Agent, or Firm*—Ostrolenk, Faber, Gerb & Soffen

[57] ABSTRACT

Antigenic compositions are disclosed for use in diagnostic kits and the like for detecting the presence of antibodies specific for *Campylobacter pylori*, bacteria often associated with the occurrence of Type B gastritis and peptic ulcer disease. Samples of bodily fluids, for instance, may be contacted with immobilized antigen which is then washed and tested for the occurrence of significant levels of antigen/antibody complex. Levels exceeding a predetermined positive threshold are indicative of antibodies to *Campylobacter pylori* in the sample tested. Kits employing the antigenic compositions of the invention preferably include means for detecting the antigen/antibody complex such as materials and reagents for conducting an enzyme-linked immunosorbent assay, Western blot technique, liposome-based assay or other known detection tests.

30 Claims, 9 Drawing Sheets

OTHER PUBLICATIONS

Wyatt et al., "Local Immune Response to Gastric Campylobacter in Non–Ulcer Dyspepsia", *J. Clin. Pathol.*, 1986; 39:863–870.

Rathbone, et al., "Systemic and Local Antibody Responses to Gastric *Campylobacter pyloridis* in Non–Ulcer Dyspepsia", *Gut*, 1986, 27, 642–647.

Jones, et al., "Campylobacter–Like Organisms on the Gastric Mucosa: Culture, Histological, and Serological Studies", *J. Clin. Pathol.*, 1984; 37:1002–1006.

Jones et al., "Antibody to the Gastric Campylobacter–Like Organism ('*Campylobacter pyloridis*')—Clinical Correlations and Distribution in the Normal Population", *J. Med. Microbiol.*, vol. 22 (1986), 57–62.

Kaldor et al., "Immunoblot Confirmation of Immune Response to *Campylobacter pyloridis* in Patients with Duodenal Ulcers", *The Medical Journal of Australia*, vol. 145, pp. 133–135 (1986).

Morris, et al., "Seroepidemiology of *Campylobacter pyloridis*", *New Zealand Medical Journal*, vol. 99, No. 809, pp. 657–659 (1986).

Goodwin et al., "Enzyme–Linked Immunosorbent Assay for *Campylobacter pyloridis*: Correlation With Presence of *C. pyloridis* in the Gastric Mucosa", *Journal of Infectious Diseases*, vol. 155, No. 3, 488–494 (1987).

Blaser et al., "Identification and Characterization of *Campylobacter jejuni* Outer Membrane Proteins", *Infection and Immunity*, pp. 276–284 (1983).

Wulffen et al., "Detection of *Campylobacter pyloridis* in Patients with Antrum Gastritis and Peptic Ulcers by Culture, Compliment Fixation Test, and Immunoblot", *Journal of Clinical Microbiology*, pp. 716–720 (1986).

Blaser, "Gastric Campylobacter–Like Organisms, Gastritis, and Peptic Ulcer Disease", *Gastroenterology*, 1987; 93:371–83.

Blaser and Perez–Perez, *Abstract D–175 to March 1987 Meeting of the American Society for Microbiology*.

Perez–Perez, et al., "Campylobacter pyloridis–Specific Serum Antibodies in Patients With Gastrointestinal Illnesses and Healthy Persons", *Abstracts of the 1987 ICAAC* (Oct. 1987), Abstract 1174.

Dunn, Perez–Perez and Blaser, "Analysis of Human Immunologic Response to *Campylobacter pyloridis* Using Two–Dimensional Gel Electrophoresis and Immunoblotting", *Abstracts of the 1987 ICAAC*, Abstract 1242 (Oct. 1987).

Perez–Perez and Blaser, "Conservation and Diversity of *Campylobacter pyloridis* Major Antigens", *Infection and Immunity*, pp. 1256–1263, vol. 55, No. 5 (May 1987).

Blaser, et al., "Campylobacter jejuni Outer Membrane Proteins are Antigenic for Humans", *Infection and Immunity*, vol. 43, No. 3, pp. 986–993 (1984).

Blaser, et al., "Human Serum Antibody Response to *Campylobacter jejuni* Infection as Measured in an Enzyme–Link Immunosorbent Assay", *Infection and Immunity*, vol. 44, No. 2, pp. 292–298 (1984).

Blake et al., "A Rapid, Sensitive Method for Detection of Alkaline Phosphatase–Conjugated Anti–Antibody on Western Blots", *Analytical Biochemistry*, 136, 175–179 (1984).

Pearson, et al., "Polyacrylamide Gel Electrophoresis of Spiral Bacteria from the Gastric Antrum", *The Lancet*, pp. 1349–1350 (Jun. 16, 1984).

Morris, et al., "*Campylobacter pyloridis* Serology Among Gastroendoscopy Clinic Staff", *New Zealand Medical Journal*, p. 820 (letter) (Oct. 22, 1986).

Hutchinson, et al., "Distribution in Various Clinical Groups of Antibody to *Campylobacter pyloridis* Detected by ELISA, Compliment Fixation and Microagglutination Tests", *Proceedings of the Third International Workshop on Campylobacter Infections*, O. Hawa, Abstract No. 112, p. 185.

Hawtin et al., "Specific IgG and IgA Responses to *Campylobacter pyloridis* in Man", *Proceedings of the Third International Workshop on Campylobacter Infections*, O. Hawa, Abstract No. 113, p. 186 (Jul. 1985).

Marshall et al., "Correlation Between Symptoms of Dyspepsia and *Campylobacter pyloridis* Serology in Western Australian Blood Donors", *Proceedings of the Third International Workshop on Campylobacter Infections*, O. Hawa, Abstract No. 114, p. 188.

Megraud et al., "Characterization of '*Campylobacter pyloridis*' by Culture, Enzymatic Profile, and Protein Content", *Journal of Clinical Microbiology*, vol. 22, No. 6, pp. 1007–1010 (1984).

Gnarpe et al., "Enzyme Amino Assay Serology for Primary Screening of Patients with *Campylobacter pyloridis*", *Clinical Immunology Newsletter*, 8:10, 1987.

McNulty et al., "The Distribution of Enseriological Response to *Campylobacter pyloridis* in the Stomach and Duodenum", *Proceedings of the Third International Workshop on Campylobacter Infections*, O. Hawa, Abstract No. 105, p. 174 (Jul. 1985).

Girdwood et al., "*Campylobacter pyloridis* in Biopsy Samples of Normal and Diseased Human Stomachs: Pathological, Serological and Bacteriological Findings", *Proceedings of the Third International Workshop on Campylobacter Infections*, O. Hawa, Abstract No. 109, p. 180 (Jul. 1985).

Marshall et al., "Pyloric Campylobacter Serology", *The Lancet*, Aug. 4, 1984, p. 281.

Newell, "Identification of the Outer Membrane Proteins of *Campylobacter pyloridis* and Antigenic Cross–Reactivity Between *C. pyloridis* and *C. jujini*", *Journal of General Microbiology*, 133, 163–170 (1987).

Kaldor et al., "Immune Response to *Campylobacter pyloridis* in Patients with Peptic Ulceration", *The Lancet*, (Apr. 20, 1985), p. 921 (letter).

Rathbone et al., "Immune Response to *Campylobacter pyloridis*", *The Lancet*, May 25, 1985, p. 1217 (letter).

Paull et al., "Serum IgG Antibody to *Campylobacter pyloridis*: Diagnostic Value and Correlations with Gastric Biopsy Findings", *American Gastroentoerological Association Annual Meeting*, Abstract 922 (A–231).

Eldridge et al., "Antibody to Spiral Organisms on Gastric Mucosa", *The Lancet*, Jun. 2, 1984, p. 1237 (letter).

Rathbone et al., "Diagnostic IgG ELISA for Gastric *Campylobacter pyloridis* Infection Using Serum Samples", *Gut*, Abstract T67 (1986).

Peterson et al., "The Role of *Campylobacter pyloridis* in Epidemic Gastritis with Hypochlorhydria", *Abstract 564* (A–141).

Wulffen et al., "Seriological Screening for *Campylobacter pylori* in Candidates for Renal Transplantation", *The Lancet*, May 16, 1987, pp. 1140–1141.

Blaser, et al., "Antigenicity of *Campylobacter jejuni* Flagellae", *Infection and Immunity*, vol. 43, pp. 47–52 (1986).

under ATCC Nos. 53722,

CAMPYLOBACTER PYLORI ANTIGENS AND USES THEREOF FOR DETECTION OF CAMPYLOBACTER PYLORI INFECTION

BACKGROUND OF THE INVENTION

Field of the Invention

This invention relates to methods for detecting the presence or absence of antibodies specific to *Campylobacter pylori,* and more particularly to the clinical use of novel antigenic compositions for detecting the presence of antibodies to *C. pylori* and/or for diagnosing certain gastrointestinal disorders.

Peptic ulcer disease, gastritis and other inflammatory gastroduodenal conditions are common maladies throughout the world. Numerous studies have indicated that there is a correlation between the presence of *C. pylori* infection and affliction with peptic ulcer disease or Type B gastritis (the most common form of gastritis). Hence, determining whether or not *C. pylori* infection is present in patients complaining of gastrointestinal symptoms can be useful in determining the likelihood that the symptoms derive from gastritis or peptic ulcer.

Most current diagnostic methods for *C. pylori* infection are costly, difficult to perform in a clinical setting, overly time-consuming and/or unduly invasive and uncomfortable for the patient. For instance, one test involves passage of a tube through the mouth and into the stomach or duodenum for obtaining a biopsy of tissue. Another test involves measuring the increase in carbon dioxide released in the breath of a patient who has consumed a solution containing urea. (*C. pylori* contain the enzyme urease, which releases carbon dioxide from ingested urea.) Costly instrumentation is required to detect this difference. An analogous test involving carbon 14-labeled urea leads to the production of carbon 14-labeled carbon dioxide that is easier to detect. However, this test is undesirable because it involves exposing the patient to a radioactive isotope.

It is known that persons infected with *C. pylori* tend to develop antibodies specific to the organism. Prior art methods for detecting these antibodies did not, however, identify specific antigenic compositions capable of providing sufficient practical utility and accuracy for widespread clinical use. Antigens which are not sufficiently unique to substantially assure that only *C. pylori*-specific antibodies are attracted render the formation of antigen/antibody complex inconclusive as to the presence of antibody to *C. pylori.* Conversely, antigens which are not common to most *C. pylori* strains or which do not produce strong immunogenic responses may not bind the *C. pylori*-specific antibodies of patients infected with certain strains. In such a case, the failure of antigen/antibody complex to form does not necessarily indicate lack of *C. pylori* infection. In the prior art, adequate sensitivity often coincided with inadequate specificity, and vice-versa. Moreover, where sensitivity is low, practical limits are placed on the degree by which the sample may be diluted. Hence, false positive signals are not as easy to eliminate as would be the case at higher dilution.

OBJECTS OF THE INVENTION

It is accordingly an object of the present invention to provide a highly specific and highly sensitive diagnostic test for the presence of *C. pylori* infection.

It is another object of the invention to provide antigenic compositions which specifically, and with high sensitivity, attract and bind to antibodies directed against *C. pylori.*

It is another object of the invention to provide a procedure to aid in diagnosis of gastrointestinal symptoms which is relatively non-invasive and causes little patient discomfort.

It is another object of the invention to provide cost-effective clinical diagnostic tests for the presence of *C. pylori* which are simple to administer in a clinical or home setting, and which may be quickly evaluated, and to provide kits for performing such diagnostic tests.

It is another object of the invention to provide a means for monitoring the effectiveness of treatments designed to reduce or eliminate *C. pylori* infection.

It is another object of the invention to provide a diagnostic test of sufficient sensitivity to utilize highly dilute test samples.

SUMMARY OF THE INVENTION

The foregoing and other objects are achieved by providing antigenic compositions which include at least fragments of *C. pylori* and have an enriched concentration of at least one fragment which exhibits exceptional antibody response, is common to most strains of *C. pylori,* and exhibit sufficient uniqueness that it is substantially unrecognized by antibodies present in non-infected individuals. The phrase "at least fragments" connotes that intact bacteria, i.e. the entire organism, may be used as well as fractional parts thereof. In certain embodiments of the invention, the composition is enriched in at least one fragment selected from the group consisting of 63,000, 57,000, 45,000 and 31,000 dalton fragments. In another embodiment, the antigenic composition has an enriched concentration of at least fragments of *C. pylori* flagella. In another embodiment, the antigenic composition comprises at least fragments of at least one strain of *C. pylori* selected from the group consisting of five isolates, denoted by inventors' I.D. Nos. 84- 180, 84-182, 84-183, 86-63 and 86-86, which have been deposited in the American Type Culture Collection (ATCC), 12301 Parklawn Drive, Rockville, Md. 20852, under ATCC Nos. 53722, 53725, 53726, 53727 and 53721, respectively, on or before Feb. 16, 1988, prior to the filing of this patent application (hereinafter referred to collectively as the "deposited strains"). This deposit assures permanence of the deposit and ready accessibility thereto in accordance with U.S. patent law, the Budapest Treaty and other applicable laws and regulations. All restrictions on the availability of the foregoing deposits to the public will be irrevocably removed upon grant of a patent based on the present disclosure.

The antigenic compositions described above, including specified antigens both individually and in combination with each other, act as antigenic compositions capable of binding *C. pylori*-specific antibodies. The antigenic compositions tend to complex with antibodies present in the systems of almost every *C. pylori*-infected individual regardless of the specific strain with which he is infected. Moreover, these antigens are seldomly recognized by antibodies present in the body fluids of non-infected individuals. Specific preferred antigens for the composition representing strong antibody detection capability include, but are not limited to, *C. pylori* fragments having an apparent molecular weight after electrophoresis on sodium dodecyl sulfate polyacrylamide gel (hereinafter "SDS-PAGE") of approximately 63,000, 57,000, 45,000 and 31,000 daltons. All apparent molecular weights reported herein are calculated from calibration curves based on relative electrophoretic migration of the following molecular weight standards: lysozyme 14,400 daltons; soybean trypsin inhibitor 21,500 daltons; carbonic anhydrase 31,000 daltons; ovalbumin 45,000 daltons; bovine serum albumin 66,200 daltons; phosphorylase B 92,500 daltons; beta-galactosidase 116,250 daltons; and myosin 200,000 daltons. Use of such a calibration curve typically enables definition of molecular weight plus or minus about 1,000 daltons in this molecular weight region. 1–2 microgram samples are applied to each lane after boiling for 5 minutes in a buffer containing sodium dodecyl sulfate (hereinafter "SDS") dithiothreitol and glycerol. The separating gel is 10 percent acrylamide and electrophoresis is performed at 35 mAmps for 2 hours at a constant temperature of 8° C. Bands are resolved using a silver stain. In certain preferred embodiments, isolated flagella of *C. pylori* and especially isolated fragments of said flagella having an apparent molecular weight of approximately 63,000, 57,000 and 31,000 daltons respectively, are used, individually or in combination with each other, as the antigen(s) of preference. The 63,000, 57,000, 45,000 and 31,000 dalton fragment from the deposited strains are found in most *C. pylori*—not just the deposited strains—and are useful in the antigenic composition of the invention regardless of the source from which they are derived. Appropriate synthetic antigens homologous to the antigenic fragments specified herein may also be used.

In accordance with the present invention, samples to be tested for *C. pylori*-specific antibody are contacted with the antigenic compositions defined herein. In preferred embodiments, the contacting is followed by determining whether the degree of antigen/antibody complex formation exceeds a threshold which indicates that the sample is positive for *C. pylori*-specific antibody. The formation of antigen/antibody complex is detected by conventional techniques. The extent of detection of the antigen/antibody complex which should be considered a positive signal (i.e., an indication that the test sample includes *C. pylori*-specific antibody) depends upon the detection means chosen, but may be defined generically as a value greater than the mean plus 1 (and preferably 3) intervals of standard deviation from the results observed from a negative control group. The negative control group should consist of asymptomatic individuals who are members of a population which is unlikely to include individuals infected with *C. pylori*. A preferred control group, for instance, is a group of asymptomatic children below 10 years of age. Such children form a population unlikely to be infected.

Preferred techniques for detecting formation of antigen/antibody complexes include, but are not limited, to enzyme-linked immunosorbent assay (ELISA), indirect fluorescence assay, and liposome-based assay. Alternatively, a Western blot technique may be used, in which case the bands are detected by visual inspection, and substantial appearance of dark bands may be taken as a positive indication.

In certain preferred embodiments of the invention, clinical kits are provided which include both antigenic compositions in accordance with the invention and a means for detecting antigen/antibody complex.

Because of the correlation between *C. pylori* infection and certain gastric disorders such as peptic ulcer and gastritis, these disorders may be diagnosed by testing for antibodies to *C. pylori* in accordance with the present invention. Moreover, follow-up testing for antibodies following treatment for *C. pylori* infection may be used to monitor the progress of such treatment. Because *C. pylori* infection may occur at widely varied physical locations in the upper gastrointestinal tract, the assays of the invention may improve on even the accuracy obtainable by endoscopy and biopsy which sample only specific areas.

The invention also provides, in certain aspects, fragments of *C. pylori* produced without increasing concentration of any particular antigen wherein the antigenic mixture is immobilized and then contacted with a test sample, and wherein the degree of formation of antigen/antibody complex is measured either by enzyme-linked immunosorbent assay or liposome-based assay. For this procedure, it is desirable, but not necessary, to enrich the antigenic mixture with one or more of the preferred antigens described herein.

As used herein, an antigenic composition is considered to be "enriched" in the concentration of one or more particular antigens whenever the concentration of the particular antigens exceeds the natural concentration (relative to other antigens) which results when *C. pylori* are extracted and fragmented under circumstances which do not selectively increase the concentration of the particular antigens.

As used herein, the term "fragment" means a portion of a bacterium resulting from disruption of the bacterial cell by common techniques for producing bacterial antigens, or synthetic homologs of said portions such as synthetic or recombinantly produced polypeptides.

BRIEF DESCRIPTION OF THE DRAWINGS

FIG. 9 depicts primarily lipopolysaccharides because proteins are digested away by proteinase K.

DETAILED DESCRIPTION OF CERTAIN PREFERRED EMBODIMENTS

Figure 1:
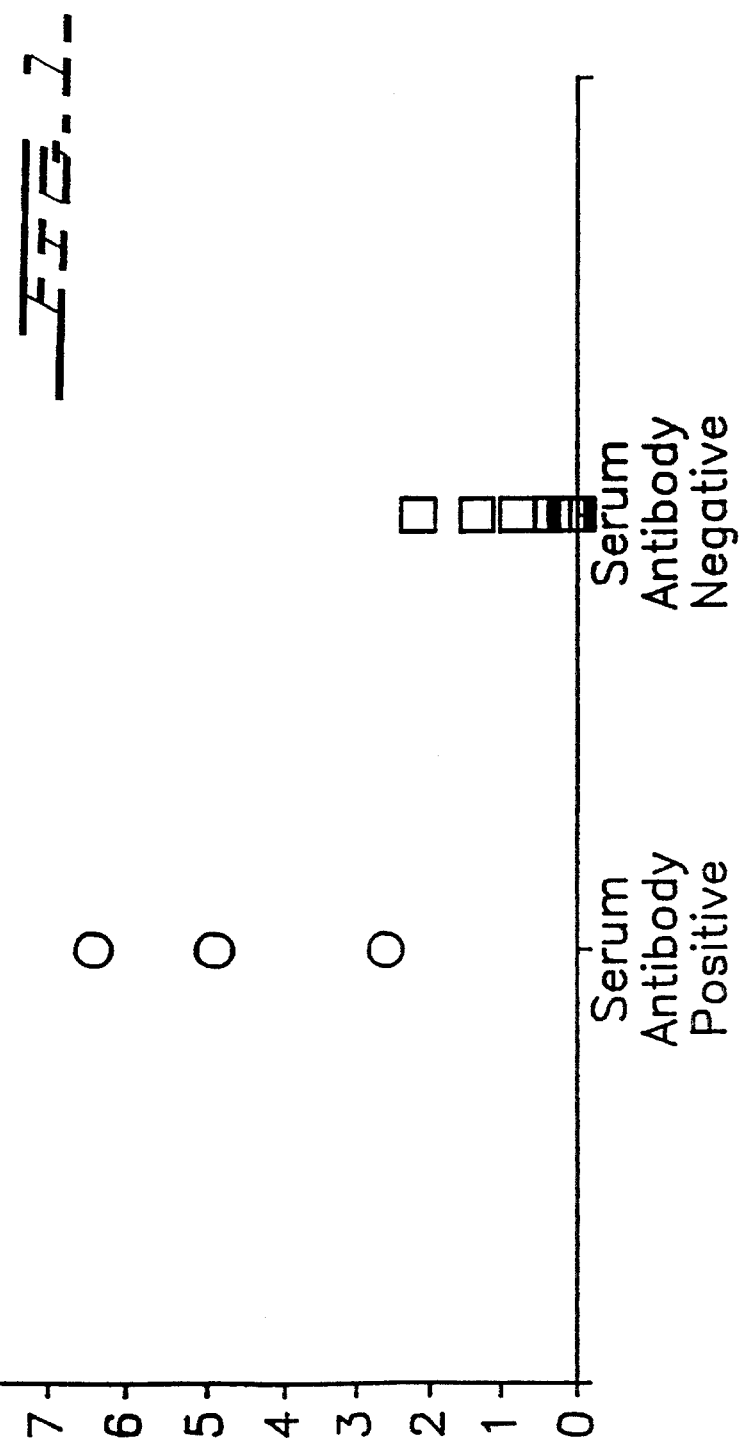
FIG. 1 illustrates the differentiation of urine specimens from persons known to be sero-positive or sero-negative for *C. pylori* infection, by measuring urinary IgG antibodies to *C. pylori*.

Any sample suspected of containing *C. pylori* antibodies may be tested in accordance with the methods set forth herein. Preferably, the samples to be tested are bodily fluids such as blood, serum, urine, tears, saliva and the like. Both medical and veterinary applications are contemplated. In addition to human samples, samples may be taken from other mammals such as non-human primates, horses, swine, etc. Due to the sensitivity of the test described, it is both possible and preferable to strongly dilute the sample prior to testing. Dilution may proceed by addition of any fluid compatible with each of the sample, the antibodies to be tested, and the immobilized antigenic composition. Serum, when used as the sample, is preferably diluted with one or more fluids selected from the group consisting of phosphate-buffered saline, pH 7.0–7.4 (hereinafter "PBS"), PBS-containing TWEEN 20 (hereinafter, "PBS T"), PBS T with thimerosal (hereinafter, "PBS TT"), PBS TT (gelatin) (hereafter "PBS TTG"), and PBS TTG with bovine gamma globulin (hereafter "PBS TTGG"), and is preferably diluted when testing for IgG antibody in a ratio from about 1:500 to about 1:1000, such as, for instance, about 1:800. Preferred dilution ratios when testing for IgA antibody are about 1:50 to about 1:200, such as 1:100. IgG tests are preferred.

Preferred diluents and dilution ratios may vary according to the sample being tested. Urine, for instance, is already relatively dilute and typically is not diluted further. However, it is unnecessary to concentrate urine as is often necessary with other assays. Prior to testing, the pH of urine is preferably adjusted to between about 7.0 and 7.4, the preferred pH for antibody function.

While dilution of sample is not required, it is believed that large dilution ratios reduce the possibility that significant antigen/antibody complexes will be formed in the absence of C. pylori-specific antibodies. The extent of dilution should be taken into account in adjusting the threshold level of antigen/antibody complex which should be considered a positive signal.

Antigenic compositions useful in accordance with the present invention include but are not limited to specific antigens isolated from fragments of the five deposited strains, one or more complete organisms from among the deposited strains, and mixtures of the foregoing. Isolated flagella, for instance, have proven to be effective antigens for the antigenic composition. Antigenic fragments of the C. pylori strains, may be characterized by their apparent molecular weight derived from their electrophoretic migration on sodium dodecyl sulfate/polyacrylamide gels as previously described. Disruption of the C. pylori organism yields inter alia proteins and lipopolysaccharides which occur in the outer membranes of gram negative bacteria.

Preferred antigenic mixtures include, isolated flagella from any C. pylori strains or fragments of said flagella, and isolated fragments of any C. pylori strains wherein the fragments have an apparent molecular weight on SDS-PAGE of 63,000, 57,000, 45,000 or 31,000 daltons. A mixture of antigens obtained from a pool of all five deposited strains is believed to include at least one antigen likely to be present in almost all C. pylori strains. Hence, a broad specificity results, enabling the antigenic mixture to be useful in serologic assays. It is preferred that the antigenic composition be enriched in flagella or in at least one of said 63,000, 57,000, 45,000 or 31,000 dalton fragments. More preferably, at least 50 percent of the composition or at least 50 percent of the C. pylori fragments are flagella or the specified molecular weight fragments. In certain preferred embodiments the concentration reaches 85 percent or more. For some applications, it may be desirable that the antigenic composition be substantially free of antigens other than flagella or the specified molecular weight fragments.

An antigenic composition is considered to be substantially free of antigens other than the antigens of interest whenever the antigenic composition, when subjected to electrophoresis on SDS-PAGE and appropriate staining, exhibits single well-defined bands corresponding to the antigens of interest, and no other bands are visually apparent.

While the present disclosure provides an easy method for obtaining the preferred antigens from the deposited C. pylori strains, it is emphasized that these antigens are common to a large number of C. pylori strains as shown by their efficacy in testing for the existence of C. pylori. While the deposited strains and the description of the present specification provide an easy manner of isolating these antigens, it is emphasized that the present invention broadly encompasses use of these antigens regardless of the source from which they are derived.

Antigenic compounds in accordance with the instant invention are preferably immobilized on a substrate using conventional techniques. For instance, polystyrene plates may be incubated with antigenic suspensions made in accordance with the invention. Alternatively, for instance, antigens isolated as protein bands on electrophoretic gel may be transferred to a nitrocellulose sheet by known methods. See Towbin et al., *Proc. Nat'l. Acad. Sci.*, 76: 4350–54 (1979); Burnette, et al., *Biochem.*, 112: 195–203 (1981). Numerous other techniques are known in the art for binding antigens to substantially inert substrates.

Bound antigens in accordance with the invention are preferably contacted with a highly dilute fluid which includes the sample to be tested for presence of antibody to C. pylori. The antigen and sample are preferably incubated for at least about one hour. Considerably less time is needed when incubation proceeds at or near human body temperature, about 37° C. Incubation at other temperatures, for instance 4° C., is also proper, but generally requires additional incubation time. Preferred incubation time at 37° C. is from about 10 minutes to about 90 minutes. The bound antigens should then be rinsed to remove any unbound antibodies, i.e., those which are not specific for the antigens. Preferably, rinsing proceeds with a buffer solution such as PBS T, PBS TT or Tris/TWEEN/Sodium chloride/azide. Multiple rinsings are preferred.

During incubation, C. pylori-specific antibodies bind to the immobilized antigens to create antigen/antibody complexes. All unbound antibodies are substantially removed during the rinsing procedure. Due to the high specificity of the antigens of the invention, antibodies which are not specific for C. pylori have been substantially removed at this point. Naturally, if the tested sample did not contain C. pylori-specific antibodies, the immobilized antigens would be substantially free of human antibody at this point and subsequent testing for antigen/antibody complexes should not indicate a substantial presence of such complexes. On the other hand, if the tested sample were rich in C. pylori-specific antibodies, these antibodies should have bound to the immobilized antigens to form a large quantity of antigen/antibody complex for subsequent detection.

Detection of antigen/antibody complex may be achieved by a wide variety of known methods. Preferred methods include but are not limited to enzyme-linked immunosorbent assay, Western blot technique or indirect fluorescence assay. In one embodiment, a liposome based assay may be used, wherein antigen recognized by C. pylori-specific antibody is expressed onto a liposome and binds C. pylori-specific antibody for subsequent detection as explained in more detail below.

Typically, the C. pylori-specific antibodies complexed with immobilized antigen are detected by contact with labelled or otherwise detectable second antibodies specific for human immunoglobulin. The labelled second antibodies may be specific for any human antibody, preferably of the IgG or IgA type, most preferably, IgG. When acute seroconversion is suspected, an IgM test may be appropriate. The second antibodies are preferably incubated with the immobilized antigens for about 15 minutes to about 2 hours, preferably 30 minutes to 60 minutes at a temperature of about 20° C. to about 37° C. Then, the antigens are washed with a buffer solution (preferably multiple times) in order to remove all unbound labelled antibody. At this point, labelled antibody has been substantially removed except where it has bound to human immunoglobulin present on the antigens. Of course, substantially the only human immunoglobulin present at this point should be C. pylori-specific antibody. Hence, the presence of C. pylori-specific antibody may be indirectly measured by determining the presence or absence of the labeled second antibody. There are many known techniques for detecting the label. For instance, fluorescein-labelled antibody may be detected by scanning for emitted light at the characteristic wavelength for fluorescein. Alternatively, an enzyme label is detected by incubation with appropriate substrate and detection of a color change. This can be determined by visual inspection or can be read automatically by a spectrophotometer set at the appropriate wavelength. In Western blotting, for example, the positive signal may be detected when an enzyme is conjugated to the second antibody. Incubation with appropriate substrate enzymatically produces a color product in the immediate vicinity of the antigenic band resolved by this process. The presence of a reactive band may be detected by visual inspection. In an indirect immunofluorescence assay, fluorescein-labeled second antibodies may be detected by fluorescence-activated detectors, or by visual inspection. A liposome-based assay may involve the presence of fluorescein, an enzyme or a substrate inside a liposome onto which surface C. pylori antigens are expressed. These liposomes are incubated with the body fluid sample to be tested, in appropriate dilution, and are thoroughly washed. Those liposomes with human immunoglobulins on their surface forming an antigen/antibody complex may be recognized by incorporating a second antibody to a specific human Ig onto the inside walls of a polystyrene tube. Those liposomes with antibody bound to the C. pylori antigens will be immobilized, and non-immobilized liposomes will be washed away. The liposomes can be lysed with, for instance, detergent, or complement, and the enzyme or substrate that was in the interior is now free to react with the complementary substrate (or enzyme) in the solution in the tube. The resulting color reaction could be detected by visual inspection or spectrophotometric color determination. Alternatively, fluorescein present could be detected by a fluorescence-activated detector.

Testing of certain antigenic pools of the invention with rabbit antiserum raised to strains not in the antigenic mixture (heterologous) indicated that the pool could detect antibodies raised to these strains, as well as detecting antibodies raised to the homologous strains. This indicated that the pool of antigens which included both the conserved and the diverse (strain-specific) antigens had the type of broad specificity which should be useful in serologic assays.

The sensitivity and specificity of the antibody detection in accordance with the present invention have been determined using serum obtained from persons from defined populations. The initial analysis was of 40 healthy children and antibody was not found in this group in the IgA assay, and only once in the IgG assay (Tables 1 and 2). This is significant because both gastritis and peptic ulcer disease are very uncommon in this population and it serves as a negative control group. The distribution of optical density values in the ELISA determination from this population were used to then establish a threshold for positivity. This is significant because the assay was then prospectively tested using high-risk and low-risk populations. Examples 1 and 2 are illustrative of the results of this assessment.

The invention is further elucidated by reference to the following examples which are set forth only as non-limiting illustrations of the invention.

EXAMPLE 1

IgG Assay Using Pooled Suspensions of Sonicates of All Five Deposited Strains in the Antigenic Composition An antigenic composition was prepared from 5 C. pylori strains (ATCC deposit numbers 53722, 53721, 53725, 53726, and 53727) which represent a diverse range of antigens. Bacterial cells were plated onto chocolate agar, then incubated for 48 hours at 35° C. in an atmosphere containing 5 percent oxygen, 10 percent carbon dioxide. 5 percent hydrogen, and the remainder nitrogen. Cells from plates were harvested in sterile distilled water (3 ml/plate), centrifuged twice at 5,000× g for 10 minutes at 25° C., and then suspended in sterile distilled water. The concentration of cells from each strain was standardized at an optical density (at 450 nanometers) of 1.5, then the suspensions were added together in equal volumes (3 ml of each). The pooled suspensions were sonicated on ice four times with a Branson sonifier (model S-75, Branson Instruments, Danbury, Conn.) for 30 seconds with 30 second rests. The preparation was then centrifuged twice at 5,000× g for 20 minutes to remove whole cells and the supernatant was centrifuged for 1 hour at 100,000× g at 4° C. (L-78 ultracentrifuge, Beckman Instruments, Inc., Fullerton, Calif.). The pellet was suspended in sterile distilled water and brought to a standard concentration of 1–2 mg/ml. Sonicates were aliquoted and frozen at −70° C. until used. For use in the ELISA, the sonicates were diluted in carbonate buffer (pH 9.6).

Flat-bottom wells of 96-well polystyrene plates such as IMMULON II available from Dynatech Laboratories of Alexandria, Va., were incubated overnight at 4° C. with the sonicate of pooled suspensions from these five selected C. pylori strains at 1.0 ug per well in 100 ul of 50 mM sodium carbonate buffer, pH 9.6. The wells were aspirated dry and then washed twice with 0.01M phosphate buffered saline (PBS, pH 7.2) with 0.05 percent Tween-20 and 0.1 mg/ml thimerosal (PBS-TT) and then washed twice with 200 ul of PBS-TT with 0.1 percent gelatin (PBS-TTG) to limit non-specific reactivity.

Samples of blood serum were prepared from numerous patients whose known C. pylori characteristics are reported in Table 1 below. 100 ul of different test serum diluted 1:800 in PBS-TTG which also includes 5 mg/ml of bovine gamma globulin (hereinafter "PBS-TTGG") was added to each of three different wells, and plates were incubated for one hour at 37° C. The wells were aspirated and washed three times with PBS-TT in order to remove unbound antibodies, and then incubated for one hour at 37° C. with 100 microtiters horseradish peroxidase-labeled goat anti-human IgG at a dilution of 1:5000 in PBS-TT containing 1 percent bovine serum albumin and 0.1 percent bovine gamma globulin. Goat anti-human IgG is a second antibody that binds with the antigen/antibody complex which should have formed only in wells exposed to positive serum, i.e., serum containing C. pylori-specific antibody. The wells were successively washed five times with PBS-TT to remove the unbound goat antibody.

A 0.1 ml sample of developing solution containing 1.0 mg of 2,2'-azino-di-(3-ethyl benzthiasoline sulfonic acid) (ABTS) per ml in McIlvain's buffer (pH 4.6) with 0.005 percent hydrogen peroxide was added to each well and incubated at 25° C. for thirty minutes.

This substrate mixture detects the peroxidase label and forms a color product which may be detected by an ELISA reader capable of detecting light at a wavelength of about 410 nm. The ELISA reader quantifies the color reading. Assays were performed in triplicate. Control wells on each plate were processed in an identical fashion, except that diluent rather than test serum was added. Absorbance readings greater than the mean +3 intervals of standard deviation for the results observed when a group of 40 healthy children under 10 years old were tested were taken as positive. The positive threshold was determined to be 0.910 units of optical density at 410 nm, where 100 microliters of developing solution is placed in the standardized flat-bottom microtiter wells identified above. The results are shown in Table 1.

TABLE 1

IgG ASSAY USING SONICATES OF ALL FIVE DEPOSITED STRAINS

| Subject | No. Positive/ No. tested | Percent Positive |
|---|---|---|
| Cases | | |
| Patients with gastrointestinal symptoms and confirmed C. pylori infection and gastritis (confirmed by culture or by identification of characteristic organisms on stained histological section | 28/29 | 96.6 |
| Asymptomatic persons with confirmed C. pylori infection and gastrititis | 28/29 | 96.6 |
| Patients with confirmed duodenal ulceration | 44/45 | 97.8 |
| Controls | | |
| Asymptomatic persons without confirmed C pylori infection | 2/61 | 3.3 |
| Asymptomatic children | 1/40 | 2.5 |

EXAMPLE 2

IgA Assay Using Pooled Suspensions of Sonicates of All Five Deposited Strains in Antigenic Composition The methods employed were identical to those indicated in Example 1 except that the test human serum was used at 1:50 dilution for IgA determinations (reflecting the lower IgA concentration in serum), and peroxidase-labelled goat anti-human IgA was used as the labeled second antibody, diluted 1:1000. The positive threshold was determined to be 0.470 units of optical density determined as in Example 1. The results are shown in Table 2.

TABLE 2

IgA ASSAY USING SONICATES OF ALL FIVE DEPOSITED STRAINS

| Subject | No. Positive/ No. tested | Percent Positive |
|---|---|---|
| Cases | | |
| Patients with gastrointestinal symptoms and confirmed C. pylori infection and gastritis (confirmed by culture or by identification of characteristic organisms on stained histological section | 28/29 | 96.6 |
| Asymptomatic persons with confirmed C. pylori infection and gastritis | 28/29 | 96.6 |
| Patients with confirmed duodenal ulceration | 45/45 | 100.0 |
| Controls | | |
| Asymptomatic persons without confirmed C. pylori infection | 3/61 | 4.9 |
| Asymptomatic children | 0/40 | 0.0 |

EXAMPLE 3

IgG Antibodies to C. pylori in Urine of Persons with Serum Antibodies to C. pylori Urine from persons known to have serum antibodies to C. pylori (as determined by the serum test of Example 1) was assessed to determine whether specific IgG antibodies were detectable in urine. The methods employed are identical to those of Examples 1 and 2 except that the pH of the urine specimen was neutralized to 7.4 using 1N sodium hydroxide and 100 ul of this specimen was added to each microtiter well. To account for differences in hydration status of the persons tested and dilution of urine, creatinine concentration of the urine specimen was measured, and the results were expressed as a ratio of optical density in the ELISA divided by the creatinine concentration. This standardizes the assay regardless of variation in concentration of urine. The results obtained from the IgG ELISA are presented in FIG. 1. There was no overlap between the values obtained from the 4 persons who were known to be sero-positive and the 10 known to be sero-negative. Using the mean +3 intervals of standard deviation for the urine specimens obtained from sero-negative persons as the cutoff for positivity, all of the sero-positive persons were positive. The threshold positive indicator (in units determined by multiplying optical density by 1,000, then dividing the product by creatinine concentration in mg per deciliter) was 2.6 units.

EXAMPLE 4

Western Blot Assay

Western blot analysis of the test sera was conducted as follows: a pool of sonicates as in Examples 1–3 was fractionated by electrophoresis on a 10 percent polyacrylamide slab gel in the presence of sodium dodecyl sulfate (SDS). The bands on the gel were electrophoretically transferred to a nitrocellulose sheet, according to the procedure of Towbin et al., (Proc. Natl. Sci. USA 76: 4350–54 (1979)) as modified by Burnette (Anal. Biochem. 112: 195–203, (1981)). Strip solid phase enzyme-immunoassays were then performed.

In brief, after SDS-PAGE, the gels were covered with nitrocellulose paper (NCP) that had been soaked in electrode buffer (192 mM glycine, 25 mM Tris base, 20 percent methanol). Electroblotting sponges were rinsed in deionized water and then saturated with the electrode buffer. After the gel was placed on the sponge, the NCP was laid over the gel, and then the second sponge was overlaid. This sandwich was placed in an electroblotting apparatus, and the proteins were electrophoresed at 100 mA for 18 hours. The NCP was rinsed in borate buffer (pH 8.0) with 0.05 percent Tween-80 and then were incubated at room temperature for one hour with 3 percent dried nonfat milk in borate buffer. After a rinsing in borate buffer, the NCP was cut into vertical strips containing multiple bands and each strip incubated at 25° C. for 4 hours in a 1:400 dilution of the test serum samples in 3 percent dried non-fat milk in borate buffer. After three one-hour washes in 1 percent dried non-fat milk in borate buffer, the NCP strips were incubated for 2 hours at 25° C. with peroxidase conjugated rabbit anti-human IgG diluted 1:5000 in 1 percent milk-borate buffer. After three twenty-minute washes in borate buffer, the NCP strips were placed in DAB solution (50 mM Tris with 0.025 percent diaminobenzidine with two drops of hydrogen peroxide), for 5 to 10 minutes until reaction products were optimally developed. The reaction was stopped by washing the strips in tap water. The strips were read by visual inspection.

Figure 5:
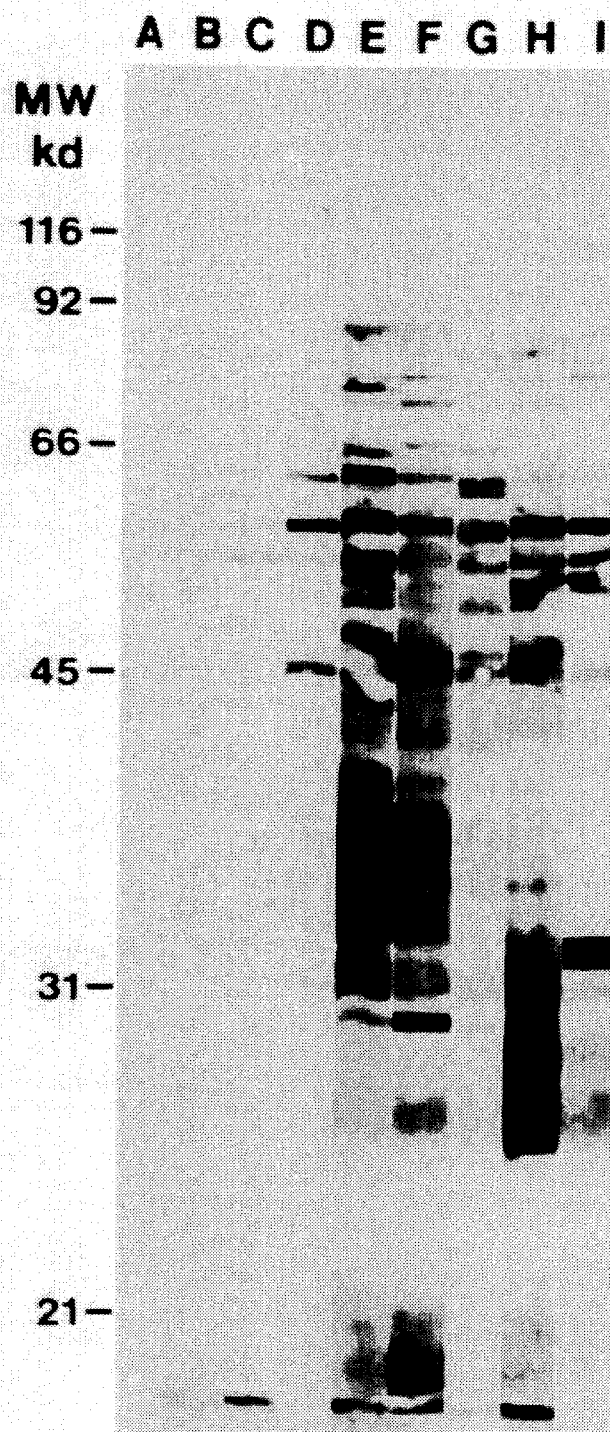
FIG. 5 relates to Example 4 and is explained therein.

FIG. 5 indicates graphically the results of these experiments. Strip A was incubated in the absence of human antibody with only 3 percent dried non-fat milk in borate buffer; Strip B was incubated with serum from a patient with gastrointestinal symptoms who had neither C. pylori infection nor gastritis; Strip C was incubated with serum from another patient with gastrointestinal symptoms who had neither C. pylori infection nor gastritis; Strip D was incubated with serum from a patient with peptic ulcer disease; Strip E was incubated with serum from a second patient with peptic ulcer disease; Strip F was incubated with serum from a patient with gastrointestinal symptoms who was found to have both C. pylori infection and gastritis by endoscopy (gastric intubation) wherein a biopsy and culture showed gastritis and presence of the organism; Strip G was incubated with serum from another patient with gastrointestinal symptoms who was found to have both C. pylori infection and gastritis; Strip H was incubated with serum from an asymptomatic person who was found to have both C. pylori infection and gastritis; Strip I was incubated with serum from another asymptomatic person who was found to have both C. pylori infection and gastritis.

EXAMPLE 5

Figure 2:
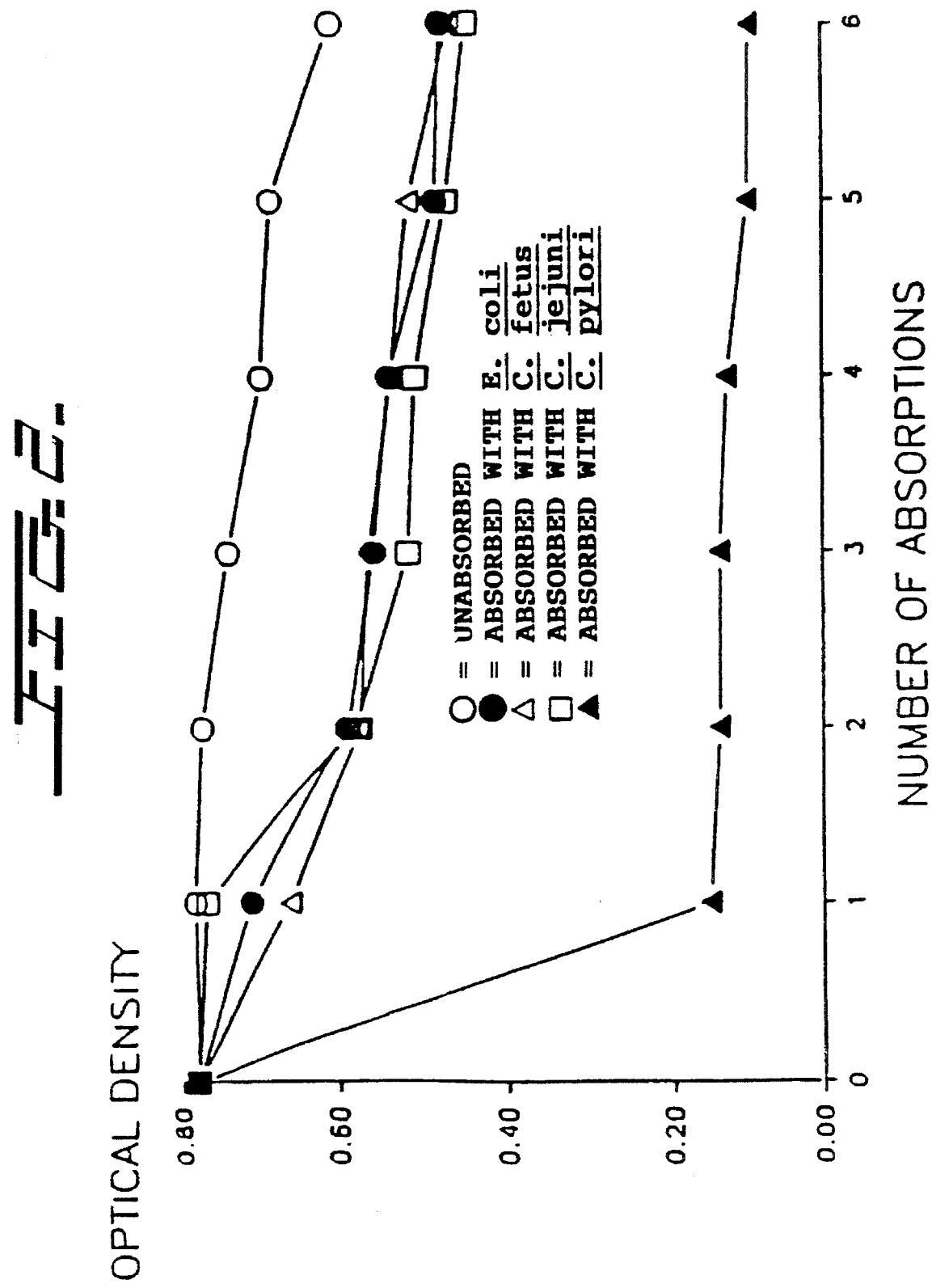
FIGS. 2–4 relate to Example 5 and are explained therein.
Figure 3:
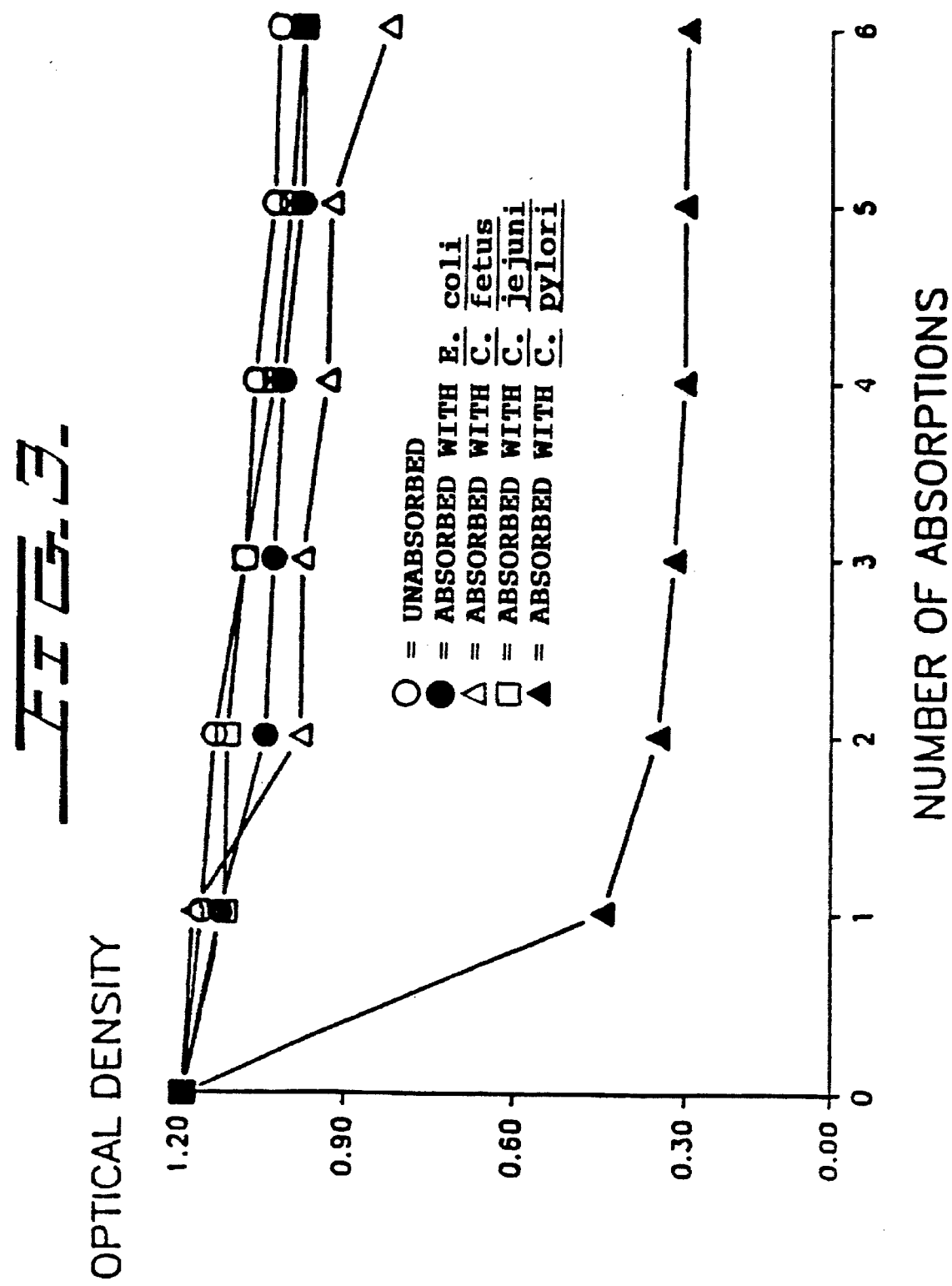
Figure 4:
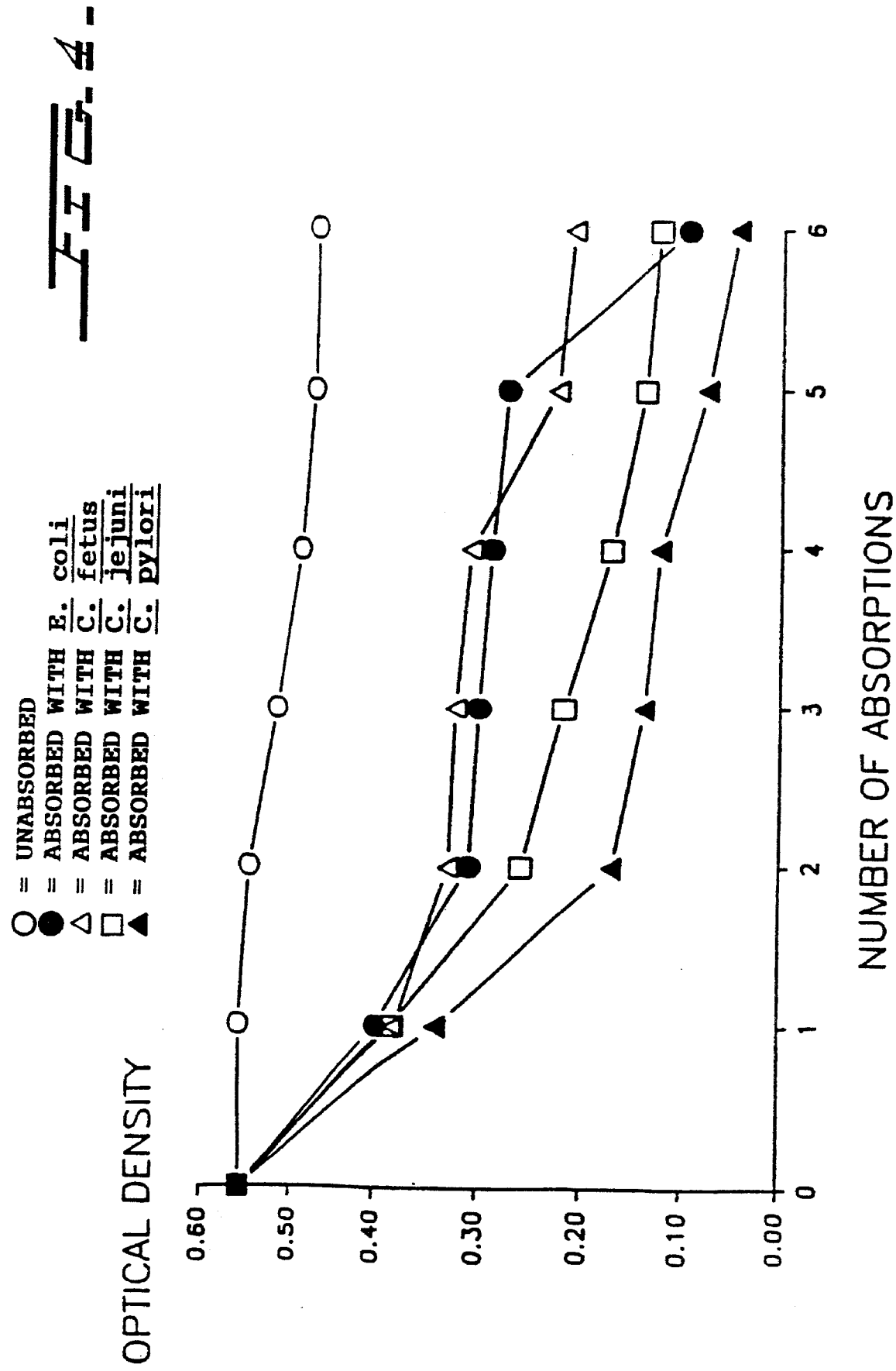

To investigate the specificity of the reactions, C. pylori cells were analyzed in comparison with cells of other enteropathogenic organisms. The assays employed determined whether pre-incubation of known positive sera in the C. pylori ELISA with C. pylori or control cells would significantly reduce optical density readings. The serum used was a pool from C. pylori-infected persons that had high values in the IgA, IgG, and IgM ELISA. The pooled serum was absorbed with whole cells of C. pylori, Escherichia coli, Campylobacter fetus, or Campylobacter jejuni. Bacterial growth from an overnight culture on one plate was harvested, cells were suspended in distilled water, washed twice with sterile distilled water, then mixed with 1.0 ml of the pooled human serum and incubated at 37° C. for 45 minutes. Antibodies to the bacterial suspension were removed by centrifugation at 12,000× g for five minutes. After saving 100 ul aliquot for ELISA determination after each absorption, the supernatant was reabsorbed five times. An unabsorbed serum control was exposed to the same incubation and centrifugation conditions. Preincubation of the positive serum pool with C. pylori cells significantly reduced optical density in all three immunoglobulin classes. Absorption of the pool with C. jejuni, C. fetus, or E. coli produced minimal decreases in optical density in the IgA (FIG. 2) and IgG ELISA (FIG. 3). However, in the IgM ELISA (FIG. 4), absorption with the homologous and heterologous organisms produced less diverse levels of inhibition. These results show that the antigens detected in the IgA and IgG are more specific for C. pylori than are those detected in the IgM ELISA.

To further define the specificity of the C. pylori ELISAs for sero-diagnosis of C. pylori infection, antibody levels in other control groups were compared. There were no seroconversions between acute and convalescent-phase specimens from 30 patients with acute bacterial enteritis with fecal leukocytes present. Included among these were 12 patients with acute C. jejuni infection, each of whom seroconverted to C. jijuni antigens.

Figure 6:
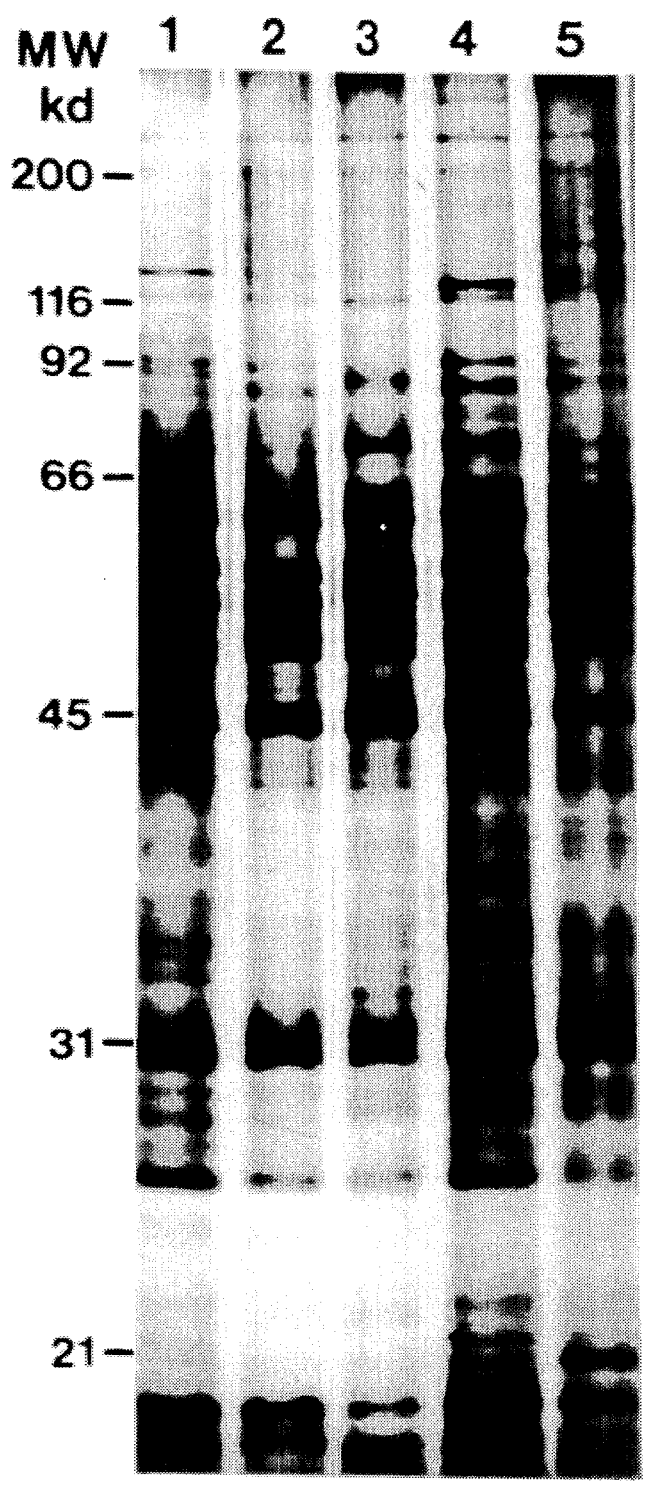
FIG. 6 is a whole cell profile of the deposited strains with strips 1–5 representing, the whole cell profile (by SDS-PAGE under denaturing conditions) of deposited strains 86-63 (ATCC 53727), 84-180 (ATCC 53722), 84-182 (ATCC 53725), 86-86 (ATCC 53721) and 84-183 (ATCC 53726), respectively.

FIG. 6 is a whole cell profile of the deposited strains with strips 1–5 representing, the whole cell profile (by SDS-PAGE under denaturing conditions) of deposited strains 86-63 (ATCC 53727), 84-180 (ATCC 53722), 84-182 (ATCC 53725), 86-86 (ATCC 53721) and 84-183 (ATCC 53726), respectively.

Figure 7:
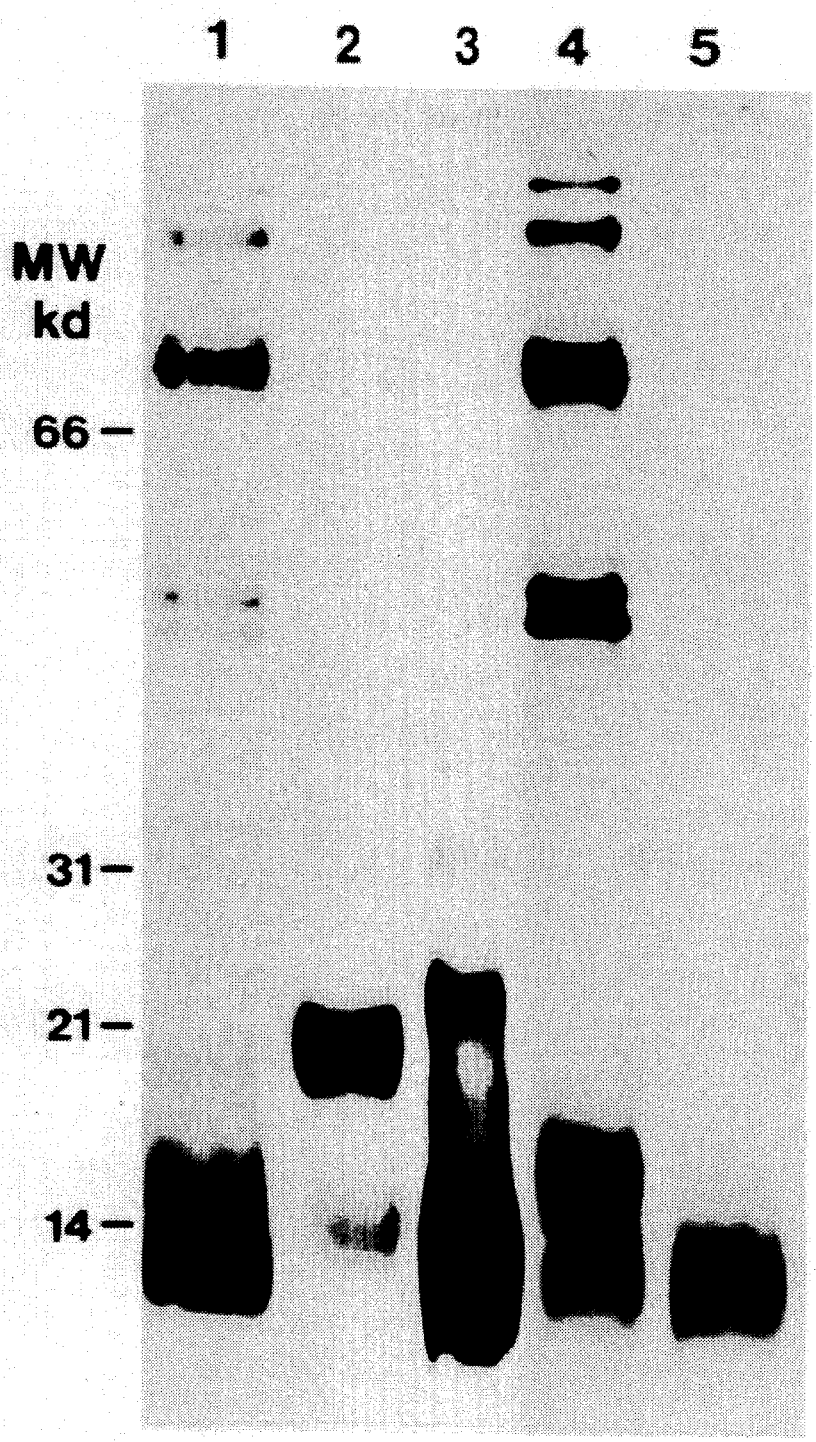
FIG. 7 is the lipopolysaccharide profile of the five deposited strains of FIG. 6, lanes 1–5 representing deposited strains 86-63 (ATCC 53727), 84-180 (ATCC 53722), 84-182 (ATCC 53725), 85-86 (ATCC 53721) and 84-183 (ATCC 53726), respectively.

FIG. 7 is the lipopolysaccharide profile of the five deposited strains of FIG. 6, lanes 1–5 representing deposited strains 86-63 (ATCC 53727), 84-180 (ATCC 53722), 84-182 (ATCC 53725), 86-86 (ATCC 53721) and 84-183 (ATCC 53726), respectively.

Figure 8:
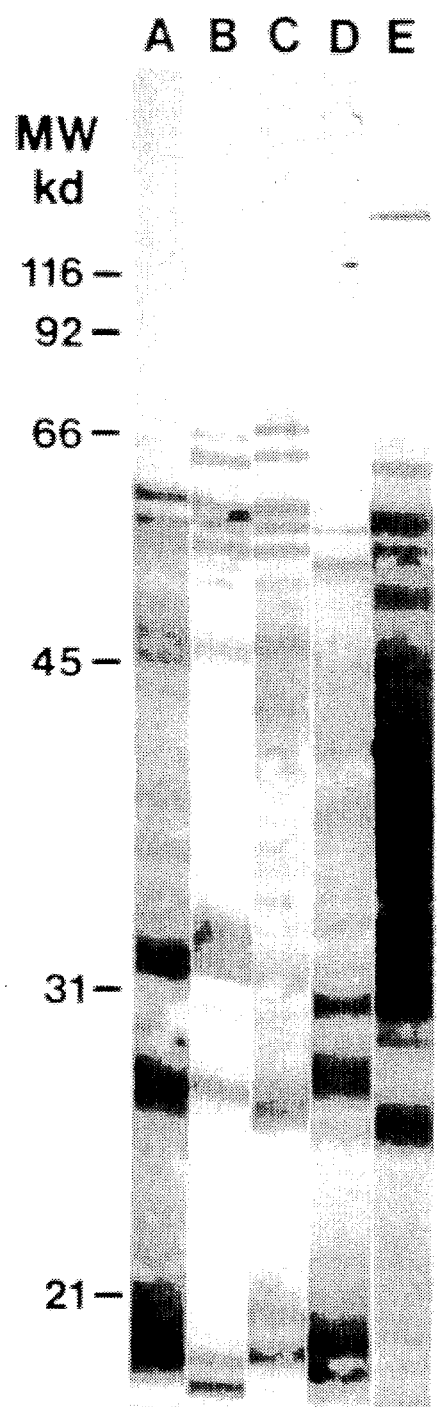
FIG. 8 is a Western blot of the deposited strains wherein each strain has been blotted with rabbit serum raised against that particular strain. For instance, strip A relates to whole cell fragments of organism A reacted with rabbit antiserum raised against organism A. Lanes A through E represent deposited strains 84-180 (ATCC 53722), 84-182 (ATCC 53725), 84-183 (ATCC 53726), 86-63 (ATCC 53727) and 86-86 (ATCC 53721), respectively.

FIG. 8 is a Western blot of the deposited strains wherein each strain has been blotted with rabbit serum raised against that particular strain. For instance, strip A relates to whole cell fragments of organism A reacted with rabbit antiserum raised against organism A. Lanes A through E represent deposited strains 84-180 (ATCC 53722), 84-182 (ATCC 53725), 84-183 (ATCC 53726), 86-63 (ATCC 53727) and 86-86 (ATCC 53721), respectively.

Figure 9:
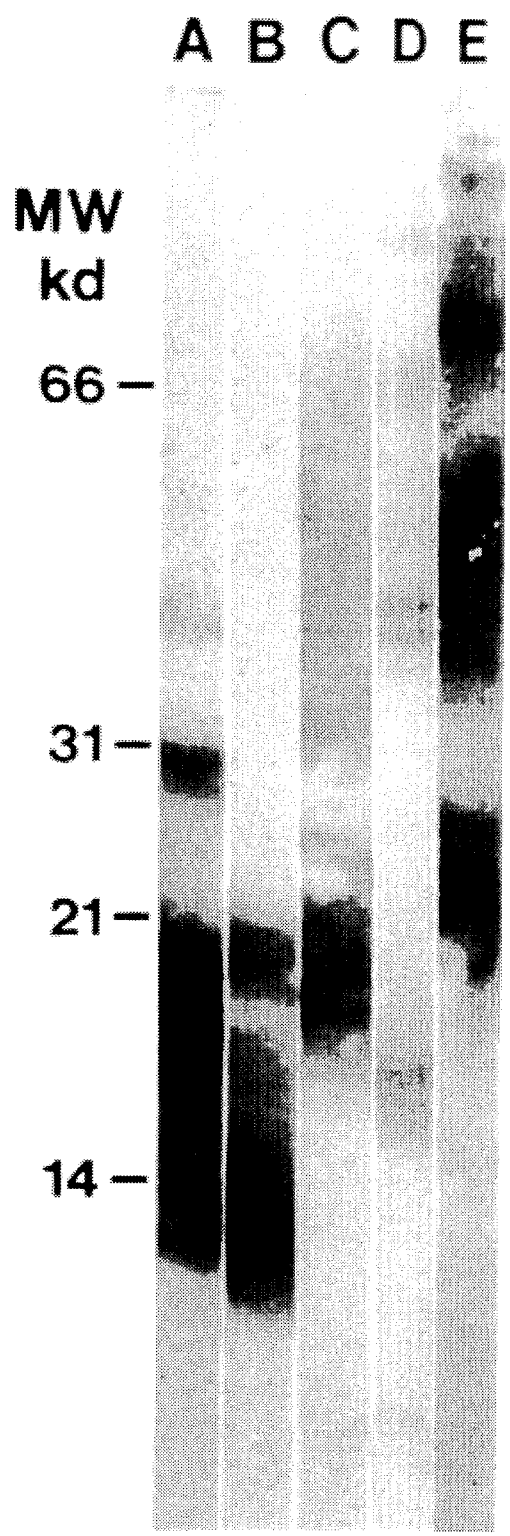
FIG. 9 is a Western blot of the five deposited strains (lanes A–E representing deposited strains 84-180 (ATCC 53722), 84-182 (ATCC 53725), 84-183 (ATCC 53726), 86-63 (ATCC 53727) and 86-86 (ATCC 53721), respectively) wherein each lane includes proteinase K-treated whole cell lysates blotted with antiserum raised against the homologous organism.

FIG. 9 is a Western blot of the five deposited strains (lanes A–E representing deposited strains 84-180 (ATCC 53722), 84-182 (ATCC 53725), 84-183 (ATCC 53726), 86-63 (ATCC 53727) and 86-86 (ATCC 53721), respectively) wherein each lane includes proteinase K-treated whole cell lysates blotted with antiserum raised against the homologous organism. FIG. 9 depicts primarily lipopolysaccharide because proteins are digested away by proteinase K.

EXAMPLE 6

Use of Single C. pylori Strain as Antigen in Assay Instead of Five-strain Pool

Strain 84-183 (ATCC 53726) was processed exactly as indicated in Example 1. However, for establishing the assay, instead of pooling sonicates from five strains to reach a protein concentration of 1.0 ug per well, the sonicate from strain 84-183 (ATCC 53726) was used alone at a concentration of 1.0 ug per well. The results of the comparison between the assays when the standard five-strain antigen was used and when the single antigen was used are shown in Table 3.

TABLE 3

Comparison of diagnostic efficacy of *C. pylori* serum ELISA using five strain sonicated (5-Ag) versus sonicates of strain 84-183 only (1-Ag).

| Patients Studied | | Number of Sera Found to Be Positive For | | | |
|---|---|---|---|---|---|
| | | IgG | | IgA | |
| Group | n | 5-Ag[a] | 1-Ag[b] | 5-Ag[c] | 1-Ag[d] |
| Known positive[e] | 14 | 14 | 14 | 14 | 14 |
| Known negative[f] | 14 | 0 | 0 | 2 | 2 |

[a]Standard assay employing five *C. pylori* strains as the antigen; optical density above 0.910 as positive threshold.
[b]Comparison assay employing one *C. pylori* strain (84-183) as the antigen; optical density above 0.700 as positive threshold.
[c]Standard assay employing five *C. pylori* strains as the antigen; optical density above 0.470 as positive threshold.
[d]Comparison assay employing one *C. pylori* strain (84-183) as the antigen; optical density above 0.470 as positive threshold.
[e]These patients had *C. pylori* present in tissue on histologic examinations, had *C. pylori* isolated from culture, and had gastritis on biopsy.
[f]These patients had no *C. pylori* present in tissue or culture, and had no gastritis.

These results indicate that choice of a single *C. pylori* strain which possesses certain conserved antigens will permit an assay to be developed that has similar or identical diagnostic efficacy as when the pooled antigen is used.

EXAMPLE 7

Use of Purified *C. pylori* Flagellae as Antigen in Assay Instead of Five-strain Pool Flagellae of gram-negative bacteria usually possess important surface antigens to which infected hosts generally produce antibodies. To determine whether any of these antigens were in fact among those to which *C. pylori*-infected persons were responding, we purified flagellae for further study.

Strain 84-182 (ATCC 53725) was grown exactly as indicated in Example 1. After the cells were harvested from plates in sterile distilled water, the suspension was centrifuged at 3,000× g for 20 minutes. The supernatant was aspirated and the pellet was resuspended in 0.1M Tris-HCl (pH 7.4) to achieve an optical density at the 450 nanometer setting of 1.5. This suspension was treated by passage at 0° C. in a Virtis blender at medium-high intensity for 45 seconds. This procedure shears the flagella from Campylobacter species (Blaser et al., *Infection and Immunity* 1986; 53: 47–52). The suspension was then centrifuged at 12,000× g for 10 minutes at room temperature to pellet cells and cell debris. The supernatant was then centrifuged at 55,000× g for 60 minutes at 5° C. to sediment the sheared flagella. This pellet was resuspended in Tris buffer at 4° C. and protein concentration determined. For establishing the ELISA, this preparation was used at protein concentrations of 100 ng per microtiter plate well. Further steps in the assay were exactly as indicated in Example 1. The results of the comparison between the IgG assays with the standard five-strain antigen was used and when the flagella preparations were used are shown in Table 4.

A strain other than the deposited strains was selected in an unbiased manner, and flagella compositions were prepared as above. These compositions were tested at 100 and 500 ng per well and the results tabulated in Table 4.

TABLE 4

Comparison of diagnostic efficacy of *C. pylori* serum IgG ELISA using five-strain sonicate versus purified flagella preparations as the antigen.

| Patients Studied | | | Number of Sera Found to Be Positive for IgG | | |
|---|---|---|---|---|---|
| | | | Separated Flagella Prep'n | Flagellar Preparation | |
| Group | n | 5-Ag[a] | 100 ng[b] | 500 ng[c] | 100 ng[d] |
| Known positive[e] | 14 | 14 | 14 | 14 | 13 |
| Known negative[f] | 14 | 0 | 0 | 0 | 0 |

[a]Standard assay employing five *C. pylori* strains as the antigen; optical density above 0.910 as positive threshold.
[b]Comparison assay employing purified *C. pylori* flagella from deposited strain 84-182 (ATCC 53725) as the antigen at a concentration of 100 ng/well; optical density above 0.080 as positive threshold.
[c]Comparison assay employing purified *C. pylori* flagellae from the non-deposited selected strain as the antigen at a concentration of 500 ng/well; optical density above 0.090 as positive threshold.
[d]Comparison assay employing purified *C. pylori* flagellae from the non-deposited selected strain as the antigen at a concentration of 100 ng/well; optical density above 0.090 as positive threshold.
[e]These patients had *C. pylori* present in tissue on histologic examinations, had *C. pylori* isolated from culture, and had gastritis on biopsy.
[f]These patients had no *C. pylori* present in tissue or culture, and had no gastritis.

EXAMPLE 8

Use of Pooled Gel Filtration Fractions of *C. pylori* Flagella as Antigen in Assay Instead of Five-strain Pool To determine which of the *C. pylori* flagellae-associated antigens were those to which *C. pylori*-infected persons were responding, a flagellar preparation from a *C. pylori* strain selected in an unbiased manner (the same such strain as in Example 7) was fractionated by passage through a gel filtration chromatographic column. The column employed was a SUPEROSE 12 column (Pharmacia Laboratories, Piscataway, N.J.) in a Pharmacia Fast Protein Liquid Chromatographic (FPLC) apparatus. The manufacturer's specification for the Superose 12 column indicates that it is a cross-linked agarose gel filtration column with an average particle size of 10 ±2 micrometer, has a globular protein exclusion limit of $2\times10^6$ daltons (optimal separation range 1000–$3\times10^5$ daltons). The column was used in accordance with the manufacturer's specifications. The flagellar preparation was suspended in 20 mM tris buffer (pH 8.0). The flow rate was 0.3 ml/min and fractions were collected over a period of 100 minutes. The first peak passed through the column between 20 and 30 minutes, and other peaks were seen after 60 minutes. Analysis of the content of the first peak was by SDS-PAGE followed by silver staining. Using this sensitive stain, only 3 bands were resolved for the fractions representing the peak. These migrated at 63,000, 57,000 and 31,000 daltons. For establishing the ELISA, these fractions were pooled, and this preparation was used at a protein concentration of 100 ng per microtiter plate well. Further steps in this assay were exactly as indicated in Example 1. The results of the comparison between the IgG assays when the standard five-strain antigen was used and when the gel filtration fractions of the flagella preparation was used are shown in Table 5.

TABLE 5

Comparison of diagnostic efficacy of *C. pylori* serum IgG ELISA using five-strain sonicate versus gel filtration of the flagella preparation as the antigen.

| Patients Studied | | | Number of Sera Found to Be Positive for IgG | |
|---|---|---|---|---|
| Group | n | 5-Ag[a] | Gel Filtration | |
| | | | Pooled Fractions[b] | |
| Known positive[c] | 14 | 14 | 14 | |
| Known negative[d] | 14 | 0 | 0 | |

[a] Standard assay employing five *C. pylori* strains as the antigen; optical density above 0.910 as positive threshold.
[b] Comparison assay employing selected fractions of *C. pylori* flagellae passed through gel filtration chromatographic column at a concentration of 100 ng/well; optical density above 0.100 as positive threshold.
[c] These patients had *C. pylori* present in tissue on histologic examinations, had *C. pylori* isolated from culture, and had gastritis on biopsy.
[d] These patients had no *C. pylori* present in tissue or culture, and had no gastritis.

EXAMPLE 9

Persistence of Serum Antibodies to *C. pylori*

Five persons with high IgA or IgG serum antibody levels to *C. pylori* were selected for further study. From each person, a second sample obtained at least one year after the original evaluation (mean 1.25 years) was restudied. The mean antibody levels in the first and second sera are shown in Table 6.

TABLE 6

Persistence of serum antibodies to *C. pylori* in 5 sero-positive persons.

| Antibody Class | Optical Density in *C. pylori* ELISA[a] | |
|---|---|---|
| | Serum 1 | Serum 2[b] |
| IgG | 1.12 ± 0.27 | 1.18 ± 0.35 |
| IgA | 1.04 ± 0.27 | 1.04 ± 0.33 |

[a] Mean ± standard error of mean.
[b] Serum 2 obtained at least one year after serum 1.

The levels in all five persons remained stable. None of the sera converted from sero-positive to sero-negative during the interval.

EXAMPLE 10

Seroconversion in a Volunteer Challenged with *C. pylori*

A human volunteer ingested *C. pylori* and developed symptoms of acute gastritis with achlorhydria (see Morris and Nicholson; American Journal of Gastroenterology, 1987; 82: 192–199). Subsequently, his symptoms cleared but he developed chronic gastritis and *C. pylori* infection persisted. Serial serum specimens were obtained and studied for antibodies to *C. pylori*. The assays for *C. pylori*-specific IgG and IgA were exactly as described in Examples 1 and 2. The assay for IgM was performed exactly as in Example 1 except that the serum was diluted 1:400 to diminish non-specific reactivity and the serum IgM was detected by a peroxidase-conjugated goat antibody specific for IgM, and the reaction developed for 60 minutes. The results are shown below in Table 7. Seroconversion in the IgA and IgG classes occurred between days 60 and 431 following experimental challenge. Although IgM seroconversion criteria have not been specifically defined, the nearly four-fold increase in optical density between day 8 and 22 after challenge, and gradual decline is significant. It is noteworthy that the increase in *C. pylori*-specific IgM is appreciably earlier in the course of the infection than either the IgA or IgG responses.

TABLE 7

Seroconversion to *C. pylori* antigens in a volunteer challenged with *C. pylori*.

| Day After Challenge | Dat After Onset of Symptoms | Optical density[a] | | |
|---|---|---|---|---|
| | | IgG[b] | IgA[c] | IgM[d] |
| 8 | 5 | 0.154 | 0.114 | 0.163 |
| 11 | 8 | 0.111 | 0.138 | 0.227 |
| 18 | 15 | 0.185 | 0.179 | 0.591 |
| 22 | 19 | 0.049 | 0.165 | 0.647 |
| 33 | 30 | 0.157 | 0.177 | 0.524 |
| 60 | 57 | 0.138 | 0.145 | 0.445 |
| 431 | 428 | >2.000 | 0.728 | 0.171 |
| 581 | 578 | >2.000 | 0.476 | 0.223 |

[a] Each value shown is the mean of triplicate determination.
[b] Serum dilution is 1:800; threshold for positive determination is 0.910.
[c] Serum dilution is 1:50; threshold for positive determination is 0.470.
[d] Serum dilution is 1:400; no threshold for positivity has been established but serum obtained 22 days after challenge shows a nearly four-fold increase over earlier samples.

EXAMPLE 11

*C. pylori*-specific test kits were constructed for detecting antibodies using several different techniques for detection. One test kit for antibody detection was comprised of a compartmented enclosure containing a plurality of wells, plates which were coated prior to use with *C. pylori* antigens, and ELISA materials for enzyme detection consisting of peroxidase-labeled goat anti-human IgG and a color change indicator consisting of ABTS in McIlvain's buffer with 0.005 percent hydrogen peroxide. Naturally, other enzymes and developers could have been used. For instance, alkaline phosphatase-labelled goat anti-human IgG could be used in conjunction with p-nitrophenyl phosphate in diethanolamine and magnesium chloride buffer.

A second test kit for detecting antibodies using the Western blot technique was comprised of a container, cover, nitrocellulose sheet, and a polyacrylamide slab gel in the presence of sodium dodecyl sulfate, surfactants, pH modifiers, dried non-fat milk and materials for enzyme detection including a color change indicator consisting of DAB in Tris with hydrogen peroxide. This Western blot analysis kit also contains peroxidase-labeled goat or rabbit anti-human immunoglobulin and a source of *C. pylori* antigens.

Another *C. pylori*-specific test kit for detecting antibodies using the indirect immunofluorescence assay may include a compartmental container with *C. pylori* antigens, human test serum, phosphate buffered saline and fluorescein-conjugated goat anti-human IgG.

Finally, a different *C. pylori* specific test kit for detecting antibodies uses liposomes and comprises a container, human test serum, fluorescent marker- (or enzyme- or substrate-) filled liposome with *C. pylori* antigens on their surface, and a surface-active agent. In this assay the container might be a pre-coated tube or well with goat anti-human IgG.

The terms and descriptions used herein are preferred embodiments set forth by way of illustration only, and are not intended as limitations on the many variations which those of skill in the art will recognize to be possible in practicing the present invention as defined by the following claims.

What is claimed is:

1. An antigenic composition for detecting the presence of antibodies to *Campylobacter pylori,* said composition comprising a purified *Campylobacter pylori* antigen having the following characteristics:
   a. said antigen is a surface structure which can be removed or purified by mechanical extraction; and
   b. said antigen resolves into bands migrating at 63,000; 57,000 and 31,000 dalton bands when electrophoresed on sodium dodecyl sulfate polyacrylamide gel;
   wherein said antigen is present in said antigenic composition at a concentration no lower than that resulting from:
      i. mechanical disruption of whole cell *Campylobacter pylori* in a non-acidic medium, followed by
      ii. removal of cell debris by centrifuging at 12,000× gravity for 10 minutes at room temperature, followed by
      iii. sedimentation of mechanically removable surface structures of said *Campylobacter pylori* by centrifuging a supernatant from step b.ii. at 55,000× gravity for 60 minutes at 5° C., followed by
      iv. subjecting a sediment from step b.iii. to size exclusion chromatography and pooling chromatographic fractions containing said antigen.

2. The antigenic composition of claim 1, wherein said antigen is present in said antigenic composition at a concentration higher than 50% by weight of said antigenic composition.

3. The antigenic composition of claim 1, wherein said antigenic composition is substantially free of *C. pylori* proteins other than said antigen.

4. A method of detecting anti-*C. pylori* antibodies in a test sample comprising the steps of:
   (A) contacting said sample with the antigenic composition of claim 1 to form, in the presence of said antibodies, *C. pylori* antigen: anti *C. pylori* antibody immunocomplexes, and thereafter
   (B) measuring the amount of said immunocomplexes formed during step (A) as an indication of the presence of said anti-*C. pylori* antibodies in said test sample.

5. A method of detecting gastritis or peptic ulcer disease correlated with the presence of *C. pylori* in a patient comprising:
   (A) obtaining a sample of a bodily fluid from said patient;
   (B) contacting said sample with the antigenic composition of claim 1 to form, in the presence of *C. pylori* antibodies, *C. pylori* antigen: anti *C. pylori* antibody immunocomplexes, and thereafter
   (C) measuring the amount of said immunocomplexes formed during step (B) and detecting said gastritis or peptic ulcer disease in said patient when said amount of the immunocomplexes exceeds that measured in a negative control population by at least one standard deviation.

6. A diagnostic kit for detecting antibodies to *Campylobacter pylori,* said kit comprising the antigen composition of claim 1, container means for connecting said antigenic composition with a sample suspected of including said antibodies and reagent means for measuring *C. pylori* antigen: anti *C. pylori* antibody immunocomplexes formed between said antigenic composition and said antibodies.

7. The kit of claim 6 wherein said measuring means comprises an enzyme labelled anti-immunoglobulin and a chromogenic substrate for said enzyme label.

8. The kit of claim 6 wherein said antigenic composition is immobilized on a substrate.

9. A diagnostic kit for detecting gastritis or peptic ulcer disease correlated with the presence of *C. pylori,* said kit comprising the antigenic composition of claim 1, container means for contacting said antigenic composition with a sample of bodily fluid suspected of including antibodies to *Campylobacter pylori,* reagent means for measuring *C. pylori* antigen: anti *C. pylori* antibody immunocomplexes formed between said antigenic composition and said antibodies; and, a negative test control reference.

10. The kit of claim 9 wherein said measuring means comprises an enzyme labelled anti-immunoglobulin and a chromogenic substrate for said enzyme label.

11. The kit of claim 9 wherein said antigenic composition is immobilized on a substrate.

12. A method for determining anti-*Campylobacter pylori* antibodies in a blood or serum sample comprising the steps of:
   a. diluting said blood or serum by at least 1:500 (sample:diluent) to form a test sample;
   b. contacting said test sample with the antigenic composition of claim 1 to form, in the presence of said antibodies, *C. pylori* antigen: anti *C. pylori* antibody immunocomplexes; and thereafter
   c. measuring the amount of said immunocomplexes formed during step (b) to determine the amount of said anti-*C. pylori* antibodies in said blood or serum sample.

13. A method for determining anti-*Campylobacter pylori* IgA antibodies in a blood or serum sample comprising the steps of:
   a. diluting said blood or serum by at least 1:500 to 1:200 (sample:diluent) to form a test sample;
   b. contacting said test sample with the antigenic composition of claim 1 to form, in the presence of said IgA antibodies, *C. pylori* antigen: anti *C. pylori* IgA antibody immunocomplexes; and thereafter
   c. measuring the amount of said immunocomplexes formed during step (b) to determine the amount of said anti-*C. pylori* IgA antibodies in said blood or serum sample.

14. A method for determining anti-*Campylobacter pylori* IgM antibodies in a blood or serum sample comprising the steps of:
   a. diluting said blood or serum sample by at least 1:400 (sample:diluent) to form a test sample;
   b. contacting said test sample with the antigenic composition of claim 1 to form, in the presence of said IgM antibodies, *C. pylori* antigen: anti *C. pylori* IgM antibody immunocomplexes; and thereafter
   c. measuring the amount of said immunocomplexes formed during step (b) to determine the amount of said anti-*C. pylori* IgM antibodies in said blood or serum sample.

15. A method for determining anti-*Campylobacter pylori* antibodies in a sample of a body fluid selected from the group consisting of urine, tears and saliva comprising the steps of:
   a. contacting said sample with the antigenic composition of claim 1 to form, in the presence of said antibodies, C. pylori antigen: anti C. pylori antibody immunocomplexes; and thereafter c. measuring the amount to said immunocomplexes formed during step (b) to determine the amount of said anti-C. pylori antibodies in said sample of said body fluid.

16. An antigenic composition for detecting the presence of antibodies to Campylobacter pylori, said composition comprising a purified Campylobacter pylori antigen that is obtainable from a process comprising the steps of:

(A) mechanically disrupting whole Campylobacter pylori cells in a non-acidic medium, followed by (B) removal of cell debris by centrifuging at 12,000× gravity for 10 minutes at room temperature, followed by (C) sedimentation of mechanically removable surface structures of said Campylobacter pylori by centrifuging a supernatant from step (B) at 55,000× gravity for 60 minutes at 5° C., followed by (D) subjecting a sediment from step (C) to size exclusion chromatography and pooling chroamtographic fractions containing said antigen that resolves into 63,000; 57,000 and 31,000 dalton bands when electrophoresed on sodium dodecyl sulfate polyacrylamide gel.

17. The antigenic composition of claim 16, wherein said antigen is present in said antigenic composition at a concentration higher than 50% by weight of said antigenic composition.

18. The antigenic composition of claim 16, wherein said antigen composition is substantially free of C. pylori proteins other than said antigen.

19. A method of detecting anti-C. pylori antibodies in a test sample comprising the steps of:

(A) contacting said sample with the antigenic composition of claim 16 to form, in the presence of said antibodies, C. pylori antigen: anti C. pylori antibody immunocomplexes, and thereafter (B) measuring the amount of said immunocomplexes formed during step (A) as an indication of the presence of said anti-C. pylori antibodies in said test sample.

20. A method of detecting gastritis or peptic ulcer disease correlated with the presence of C. pylori in a patient comprising:

(A) obtaining a sample of a bodily fluid from said patient;

(B) contacting said sample with the antigenic composition of claim 16 to form, in the presence of C. pylori antibodies, C. pylori antigen: anti C. pylori antibody immunocomplexes, and thereafter (C) measuring the amount of said immunocomplexes formed during step (B) and detecting said gastritis or peptic ulcer disease in said patient when said amount of the immunocomplexes exceeds that measured in a negative control population by at least one standard deviation.

21. A diagnostic kit for detecting antibodies to Campylobacter pylori, said kit comprising the antigen composition of claim 16, container means for connecting said antigenic composition with a sample suspected of including said antibodies and reagent means for measuring C. pylori antigen: anti C. pylori antibody immunocomplexes formed between said antigenic composition and said antibodies.

22. The kit of claim 21 wherein said measuring means comprises an enzyme labelled anti-immunoglobulin and a chromogenic substrate for said enzyme label.

23. The kit of claim 21 wherein said antigenic composition is immobilized on a substrate.

24. A diagnostic kit for detecting gastritis or peptic ulcer disease correlated with the presence of C. pylori, said kit comprising the antigenic composition of claim 16, container means for contacting said antigenic composition with a sample of bodily fluid suspected of including antibodies to Campylobacter pylori, reagent means for measuring C. pylori antigen: anti C. pylori antibody immunocomplexes formed between said antigenic composition and said antibodies; and, a negative test control reference.

25. The kit of claim 24 wherein said measuring means comprises an enzyme labelled anti-immunoglobulin and a chromogenic substrate for said enzyme label.

26. The kit of claim 24 wherein said antigenic composition is immobilized on a substrate.

27. A method for determining anti-Campylobacter pylori antibodies in a blood or serum sample comprising the steps of:

a. diluting said blood or serum by at least 1:500 (sample:diluent) to form a test sample;

b. contacting said test sample with the antigenic composition of claim 16 to form, in the presence of said antibodies, C. pylori antigen: anti C. pylori antibody immunocomplexes; and thereafter c. measuring the amount of said immunocomplexes formed during step (b) to determine the amount of said anti-C. pylori antibodies in said blood or serum sample.

28. A method for determining anti-Campylobacter pylori IgA antibodies in a blood or serum sample comprising the steps of:

a. diluting said blood or serum sample by at least 1:50 to 1:200 (sample:diluent) to form a test sample;

b. contacting said test sample with the antigenic composition of claim 16 to form, in the presence of said IgA antibodies, C. pylori antigen: anti C. pylori IgA antibody immunocomplexes; and thereafter c. measuring the amount of said immunocomplexes formed during step (b) to determine the amount of said anti-C. pylori IgA antibodies in said blood or serum sample.

29. A method for determining anti-Campylobacter pylori IgM antibodies in a blood or serum sample comprising the steps of:

a. diluting said blood or serum sample by at least 1:400 (sample:diluent) to form a test sample;

b. contacting said test sample with the antigenic composition of claim 16 to form, in the presence of said IgM antibodies, C. pylori antigen: anti C. pylori IgM antibody immunocomplexes; and thereafter c. measuring the amount of said immunocomplexes formed during step (b) to determine the amount of said anti-C. pylori IgM antibodies in said blood or serum sample.

30. A method for determining anti-Campylobacter pylori antibodies in a sample of a body fluid selected from the group consisting of urine, tears and saliva comprising the steps of:

a. contacting said sample with the antigenic composition of claim 16 to form, in the presence of said antibodies, C. pylori antigen: anti C. pylori antibody immunocomplexes; and thereafter c. measuring the amount to said immunocomplexes formed during step (b) to determine the amount of said anti-C. pylori antibodies in said sample of said body fluid.

* * * * *